United States Patent [19]

Schiwiora et al.

[11] Patent Number: 4,632,659
[45] Date of Patent: Dec. 30, 1986

[54] PRECISION ATTACHMENT FOR SECURING DENTAL PROSTHESES

[75] Inventors: Harry Schiwiora, Pforzheim; Willi Ahr, Birkenfeld, both of Fed. Rep. of Germany

[73] Assignee: Degussa Aktiengesellschaft, Frankfurt am Main, Fed. Rep. of Germany

[21] Appl. No.: 726,236

[22] Filed: Apr. 23, 1985

Related U.S. Application Data

[63] Continuation-in-part of Ser. No. 607,131, May 4, 1984, abandoned.

[30] Foreign Application Priority Data

May 6, 1983 [DE] Fed. Rep. of Germany ....... 3316606

[51] Int. Cl.[4] .......................................... A61C 13/265
[52] U.S. Cl. .................................................... 433/181
[58] Field of Search ................. 433/182, 181, 190, 191

[56] References Cited

U.S. PATENT DOCUMENTS 2,016,511 10/1935 Oppenheimer ...................... 433/181
3,535,787 10/1970 Korte ................................... 433/182

FOREIGN PATENT DOCUMENTS 424085 5/1967 Switzerland ........................ 433/181

Primary Examiner—John J. Wilson
Attorney, Agent, or Firm—Cushman, Darby & Cushman

[57] ABSTRACT

Attachment device for dental prostheses includes male and female members with said male member including an elongated matrix member having a wall in which is formed a slot with a tongue defining the outside wall of the slot with the tongue being bendable to change the size of the slot and to provide resistance to relative movement between the male and female members when the male member is inserted into the female member; the tongue and slot are located in the middle section of the male member which comprises approximately 20 to 40 percent of the length of the male member.

2 Claims, 2 Drawing Figures

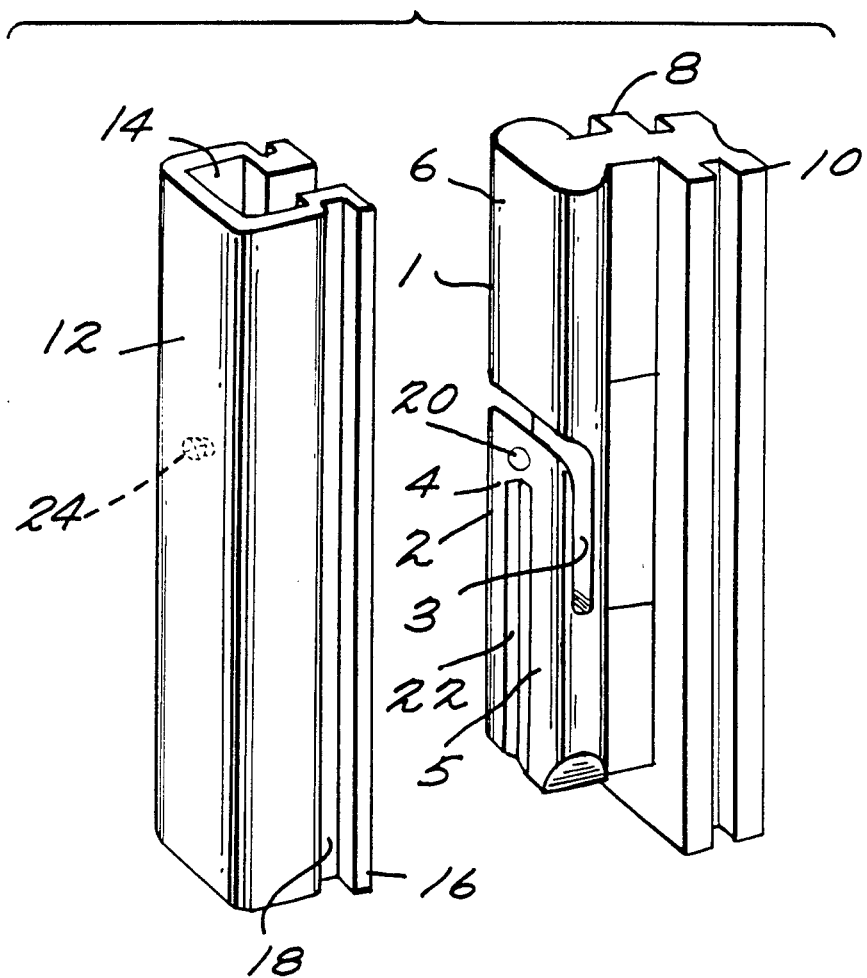

PRECISION ATTACHMENT FOR SECURING DENTAL PROSTHESES

This application is a continuation-in-part of application Ser. No. 607,131, filed May 4, 1984 and now abandoned.

BACKGROUND OF THE INVENTION

The invention is directed to a T-shaped precision attachment for detachably securing dental prostheses and bridges to the remainder of dental work including an attachment matrix member and an attachment male member that is provided with an activatable slot.

T-shaped precision attachment devices are used in dental prosthetics in order to secure prostheses and removable bridges to the remainder of the dentures or to fixed crowns or bridges. In the past, they have included various differently shaped attachment devices in an attempt to obtain secure seating of the members. Generally, the attachment matrix body member is slotted away from either the occlusal or the gingival sides. By widening this slot with special tools, the lamina formed by the slot are bent apart whereby the insertion of the male part into the attachment matrix produces an additional frictional contact in addition to the more or less exact snug fit in the matrix and thus assuring an even more secure seating. This process is designated "activation". The place of connection between the rest of the denture and the removable prostheses is a region which is especially strongly stressed in the mouth of a patient.

As a result of rotation of the attachment devices around the transverse axis of the slot, the slot is gradually compressed thus causing loosening of the seating of the attachment device. This occurs whether the slot is in the occlusal or the gingival region of the male part. As a result, the prostheses is frequently undone and can be lost. To avoid this, the attachment devices must be "activated" again at frequent intervals.

It is an object of the present invention to provide a precision attachment for detachably securing dental prostheses and bridges on the rest of the denture consisting of a male and female member with the male member being provided with an activatable slot positioned so that it avoids the foregoing difficulty.

SUMMARY OF THE INVENTION

The object of this invention is attained by positioning the activatable slot in the middle region of the male member with the middle region occupying 20 to 40 percent of the total length of the male attachment part and the slot free occlusal region constituting 30 to 55 percent and the slot free gingival region of the male member occupying 20 to 45 percent of the total length of attachments male part. Preferably, the middle, activatable region of the attachments male part makes up 25 to 40 percent of the entire region of the attachments male part.

The activation system of the male attachment member is in the middle region of the supported attachments male part body and is propped by the occlusal and gingival regions, above and below, respectively, and therefore is subjected to relatively little strain. During mastication the resulting forces acting on the attachment device from various directions or axes will not deform the activated slot to result in loosing of the attachment. Thus, visits to a professional to readjust the attachment devices to maintain a good fit of the prostheses are greatly minimized.

The position of the activation region of the male attachment parts body between the two solidly constructed, supporting occlusal and gingival regions moreover guarantees an optimum hygiene since the occlusal area of the attachment member has no slot exposed even if the attachment is shortened. With the closed attachment, no food residue can get into the activation slot or between the male and female attachment members.

As is well understood in this art, a number of well known materials are available for the production of the attachments used with this invention such as gold and platinum alloys.

BRIEF DESCRIPTION OF THE DRAWINGS

FIG. 2 is a perspective view of the male member of the attachment and the female member of the attachment.

DETAILED DESCRIPTION OF THE INVENTION

Figure 1:
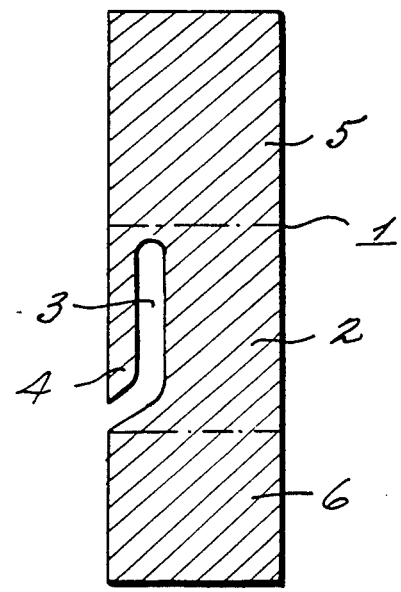
FIG. 1 is a schematic illustration of the disposition of the activatable slot in a male member.

Referring now more specifically to the drawings, the male member body 1 is divided into three regions: a middle region 2, an occlusal region 5 and a gingival region 6. In the middle region 2 there is located an activatable slot 3 in which there is formed a bendable tongue 4 defining one wall of the slot 3 and which can be activated with a suitable tool. One manner of activating the tongue 4 is simply to insert a tool into the slot 3 and then bend the tongue 4 slightly outwardly thereby widening the slot 3.

Referring now the FIG. 2, it will be seen that the male member 1 is provided with anchoring ribs 8 and 10, as illustrated, which will be securely embedded and affixed to a dental prothestic device such as a bridge, crown or the like. The female member 12 is formed with a rigid body and has a channel 14 which snuggly fits the exterior surface of the male member 1 so that where the tongue 4 has been displaced, as described above, frictional resistance to insertion of the male member 1 into the channel 14 will result thus assuring a secure fit. By locating, as described above, the slot 4 in the middle region of the member 1 between its opposite ends, many of the forces during use which normally loosen the fit of the member 1 in the channel 14 are eliminated. As an example, during mastication, rotation about a central axis which extends traverse to the longitudinal axis of the member 1 with the member 1 inserted into channel 14 does not cause premature loosening of the connection achieved by the displacement of the tongue 4 outwardly to widen the slot 3.

The length of the body 1 can be shortened from the occlusal side between 30 to 40 percent without impairing its function of effecting secure attachment between a removable dental prostheses and a fixed crown in the mouth of a patient. With the ability of such shortening, it will obviously be more comfortable to install the attachment device of the present invention in the mouth of a patient. In order to provide a good guidance of male and female members upon putting the parts together, the female member (12) is provided with a tenon (24), said tenon sliding in a slit (22) provided therefore in the male member according to FIG. 2, and reaching its final position by snapping in to a cavity (20) provided therefore in the tongue (4) of the male members middle region according to FIG. 2.

In addition to the foregoing advantages, by locating the slot 3 in the middle portion of the body 1 and with the occlusal region 5 and gingival region 6 being solid as shown, accumulation of food residue in the slot 3 will be avoided when the member 1 is inserted into the slot or channel 14 of the female member 12.

The female member 12 is provided with side flanges, one of which is indicated at 16 as well as associated channels 18 to assist in achoring the female member at a fixed prosthesis part in the mouth of a patient.

Having described the invention, it will be apparent that various modifications may be made thereto without departing from the spirit and scope of this invention as defined in the appended claims.

What is claimed is:

1. An attachment device for detachably securing a dental prosthesis in the mouth of a patient comprising a male matrix member and a female matrix member for receiving said male matrix member, said male matrix member including a portion insertable into said female member, said portion including a wall having a middle section, a gingival section on one side of said middle section and an occlusal section on the opposite side of said middle section, said female matrix member having a body including a channel shaped to closely fit over said portion of the said male member, said wall of said portion of said male member having formed therein a slot with a tongue forming one side of said slot, said tongue being bendable to change the size of said slot to provide resistance to relative movement between said male and female members, said insertable portion having a selected length and said middle section comprising from 20 to 40 percent of said selected length, said occlusal section comprising between 30 to 55 percent of said selected length, said gingival section comprising between 20 to 45 percent of said selected length, and said body of said female member having a length to substantially cover said insertable portion whereby ingress of foreign material into said slot when said prosthesis is in use will be substantially prevented.

2. The device as claimed in claim 1 wherein said middle section is between 25 to 40 percent of said selected length.

* * * * *